(12) United States Patent
Tveit (10) Patent No.: US 9,737,231 B2
(45) Date of Patent: Aug. 22, 2017

(54) BRAIN SIGNAL-BASED INSTANT SEARCH

(71) Applicant: Amund Tveit, Trondheim (NO)

(72) Inventor: Amund Tveit, Trondheim (NO)

(73) Assignee: Memkite AS, Trondheim (NO)

( * ) Notice: Subject to any disclaimer, the term of this patent is extended or adjusted under 35 U.S.C. 154(b) by 660 days.

(21) Appl. No.: 14/201,828

(22) Filed: Mar. 8, 2014

(65) Prior Publication Data

US 2015/0250401 A1 Sep. 10, 2015

(51) Int. Cl.
*A61B 5/00* (2006.01)
*A61B 5/0484* (2006.01)
*A61B 5/048* (2006.01)
*A61B 5/0482* (2006.01)
*A61B 5/16* (2006.01)

(52) U.S. Cl.
CPC .......... *A61B 5/04842* (2013.01); *A61B 5/048* (2013.01); *A61B 5/0482* (2013.01); *A61B 5/165* (2013.01); *A61B 5/4064* (2013.01); *A61B 5/7275* (2013.01)

(58) Field of Classification Search
CPC ... A61B 5/04842; A61B 5/4064; A61B 5/165; A61B 5/048; A61B 5/0482; A61B 5/7275
See application file for complete search history.

(56) References Cited

U.S. PATENT DOCUMENTS

| 2011/0238685 A1* | 9/2011 | Garcia Molina .... A61B 5/0476 707/769 |
| 2013/0012829 A1* | 1/2013 | Jo ...................... H04N 13/0429 600/544 |

OTHER PUBLICATIONS http://www.library.illinois.edu/bix/pdf/genguide/searchtips.pdf. "Tips for Searching Article Databases" University of Illinois Biology Library. Nov. 9, 2009.*
http://aberdeenunilibskills.pbworks.com/f/HeinOnline%20search%20form.pdf. "Subject Searching HeinOnline". Jun. 2011.*
https://web.archive.org/web/20130323062511/http://ishback.com/mentalspace. "The Mental Space: A speculation on mind interface design". Mar. 23, 2013.*

* cited by examiner

*Primary Examiner* — Christine H Matthews
*Assistant Examiner* — Joshua D Lannu
(74) *Attorney, Agent, or Firm* — Catherine Napjus; Michael Persson; Lawson, Persson & Chisholm, PC (57) ABSTRACT

The system of the present invention includes at least one brain signal capturing device, at least one memory device for storing software instructions, and at least one processor. The processor is in communication with the brain signal capturing device and executes the instructions stored on the memory. The instructions include the steps of analyzing a user's brain signal patterns and searching based on the user's brain signals.

56 Claims, 6 Drawing Sheets

BRAIN SIGNAL-BASED INSTANT SEARCH

FIELD OF THE INVENTION

The present invention relates to searching, and in particular, to brain signal-based instant searching for mobile devices.

BACKGROUND

Consumer-Targeted Brain-Computer Interfaces (CTBCI) started appearing in 2003 with the game marketed under the trademark MINDBALL provided by the company doing business as Interactive Productline. The purpose of the MINDBALL game was to move a ball using your brain. In 2007 CTBCIs started supporting programmatic use of captured brain signals with introduction of the headset marketed under the trademark MINDSET by the company doing business as NeuroSky. Since 2007 several new CTBCI products have appeared, including those marketed under the trademarks MELON headband (2013), XWAVE headset (2011) and MYNDPLAY BRAINBAND (2011). In addition, derived hardware products using CTBCI technology have been introduced to the market, including those marketed as follows: MATTEL MINDFLEX (2009), UNCLE MILTON STAR WARS FORCE TRAINER (2009), and NEUROSKY NECOMINI mind-controlled cat ears (2011).

In 2012, the company doing business as NeuroSky launched the mobile platform marketed under the trademark MINDWAVE, which supported programming mobile apps to use capture and use brain signals. The physical size and weight of CTBCIs are continuously decreasing, making them more comfortable to wear. An example of a recent, smaller and more comfortable CTBCI is a headband marketed under the trademark MELON, which was launched in 2013. The communication between the CTBCI and a computer (e.g. a mobile phone) is typically done using low radiation blue tooth.

Both the MINDBALL game and the MINDSET headband, discussed above, allowed capturing of electroencephalography (EEG) from the brain, i.e. electrical activity along the brain scalp. Later CTBCIs also started capturing electromyography (EMG) signals, i.e. muscle movements, and electrooculography (EOG) signals, i.e. facial expressions or eye blinks. Such developments are exemplified in the 2009 introduction by the company doing business as Emotiv of its headset marketed under the trademark EPOC and the 2010 introduction by NeuroSky of its new version of its MINDSET headset.

Since the MINDBALL game release in 2003 and until now, many of CTBCI applications have been within games or entertainment, e.g. controlling physical devices such as robots, helicopters or cat ears, or virtual characters or objects in computer games, typically with relatively simple behavior (e.g. moving the helicopter up and down). Other applications include measuring and help improving wellness, e.g. measuring brain activity for meditation support. More expensive medical brain-computer interfaces have been used to control prosthetics (e.g. robotic arms and legs), and also being able support brain-to-brain communication by enabling one person to control body parts of another person. Common for several of the medical brain-computer interfaces is that they are impractical to use outside a clinical setting. MRI requires large magnets and equipment to work, for example, and intracranial recording requires surgery.

Based on calculations of EEG, EMG, and other signals captured the CTBCI vendors have created their own derived signals, which provide estimates of higher-level mental and conscious activity in the brain. The NeuroSky mobile platform, for example, provides derived signals "Attention" and "Meditation," both measured in percentage—0 to 100%.

The goal of instant search is to provide the best search result for a query as instantaneously as possible, typically faster than 200 milliseconds. A query may have several forms, e.g. a complete sentence, several query terms or phrases, or a single or multi-character prefix. In the latter case the search engine tries to predict the most likely terms or phrases that the character prefix is likely to represent, and then provides the highest ranked answer for the most likely term or phrase. The most common way for a user to perform instant search is by typing the search query on a physical keyboard or on virtual keyboard, such as a touch-sensitive screen.

Heretofore, the advantages of inexpensive CTBCI have not been used in combination with instant search. Therefore there is a need for providing brain-controlled instant search on devices, particularly mobile devices.

SUMMARY OF THE INVENTION

The present invention is a system for analyzing a user's brain signals and allowing the user to search with his brain signals, and a computer implemented method for searching using a user's brain signals.

In its most basic form, the system of the present invention includes at least one brain signal capturing device, at least one memory device for storing software instructions, and at least one processor. The processor is in communication with the brain signal capturing device and executes the instructions stored on the memory. The instructions include the steps of analyzing a user's brain signal patterns and searching based on the user's brain signals.

The brain signal capturing device is preferably any device currently used in the art for capturing brain signals. Examples include a plurality of electrodes that may be affixed to a user's scalp, electrodes implanted in a user's brain, headbands (such as those sold under the trademarks MELON headband and MYNDPLAY BRAINBAND), headsets (such as those sold under the trademarks XWAVE headset and NEUROSKY MINDWAVE), and other CTBCI. The preferred brain signal capture device is lightweight and is neither dislodged through the user's movements, nor impedes a user's movements. The brain signal capture device may be incorporated into common head garments, such as glasses, caps, helmets, hats, sweatbands, hair bands, etc. . . . . The device captures at least EEG, and preferably also EMG and/or EOG, signals. Several types of brain waves are detected by EEG, including Low Alpha, High Alpha, Low Beta, High Beta, Low Gamma, High Gamma, Delta, and Theta. As used herein, the term "brain signals" includes EEG, including Low Alpha, High Alpha, Low Beta, High Beta, Low Gamma, High Gamma, Delta, and Theta; EMG; EOG; and other related brain signals, as well as signals derived from such signals, as discussed in the Background section and in the Detailed Description section below, in relation to Fourier transforms and kernel methods. As used herein, the term "motion signals" refers to signals provided by the movement of the user's head, such as the head's position, orientation, speed, direction, and acceleration, using for example, a gyrometer or gyroscope. In some embodiments, the device may capture motion signals of the user's head, in addition to EEG alone or in combination with other brain signals. The device is in communication with the processor such that it can relay the brain signals to the processor. This communication may be by any means commonly used in the art, such as wired or wireless.

The processor and memory device may be any commonly used in the art. The processor and memory may, for example, be part of a desktop computer, laptop computer, tablet, smartphones, or other mobile devices. It is preferred that the processor is part of a mobile device. In addition, the processor and memory may be integrated into various body implants, such as neural, sensory, spinal, organ stimulation, subcutaneous, dental, or other body implants. One of at least ordinary skill in the art will recognize that the processor and memory may be part of any of a wide variety of devices in use today, and that may be developed in the future.

The first step in the most basic form of the present invention is analyzing the user's brain signal patterns. In order to use the system of the present invention to search efficiently, a user must train using the system. In addition, the system needs to learn about the user's brain patterns, signals, and ability to control signals.

In preferred embodiments, the step of analyzing the user's brain signal patterns includes the steps of displaying to the user a sequence of images, detecting the user's brain signals as he views the sequence of images, analyzing the user's brain signals, and associating the user's brain signals with user intentions. The sequence of images may be a sequence of pictures, a sequence of letters, a sequence of words, or any other visual sequence that will promote a measurable and variable response in the user's brain patterns. The step of detecting the user's brain signals preferably includes measuring all EEG signals and derived signals produced by the user and detected by the brain signal capturing device while the user views the sequence of images. The step of analyzing the user's brain signals preferably includes detecting underlying frequencies in the user's brain signals using a Fourier transform and transforming the user's brain signals into even more derived signals using kernel methods. The Fourier transform method used is preferably either fast Fourier transform (FFT) or discrete Fourier transform (DFT). The kernel method used is preferably the radical basis function (RBF) kernel. The step of associating the user's brain signals with user intentions may include associating a specific combination of measured EEG signals and derived signals produced by the user while viewing a specific image in the sequence of images with the position of a specific image viewed within the sequence. In the case where the sequence of images is the English alphabet, for example, a specific combination of signals may imply that the user is thinking about a particular letter position, such as the fifth position, or the letter "E."

The second step in the most basic form of the present invention is searching based on the user's brain signals. Once the user has trained using the system, and the system has learned to recognize the user's brain signals, the user may use the system for instant search capabilities.

In a preferred embodiment, the step of searching based on the user's brain signals includes the steps of detecting the user's brain signals, interpreting the user's brain signals as at least one character of a search query, performing a search based on the at least one search query, and generating a search result. This preferred embodiment of the searching step of the system of the present invention is also the most basic form of the computer implemented method of the present invention. This embodiment and all further embodiments discussed below are therefore both a part of the system and method of the present invention.

The step of detecting the user's brain signals involves the computer or processor receiving the brain signals from the brain signal capturing device. The step of interpreting the user's brain signals as at least one character of a search term preferably includes the steps of providing a set of ordered characters and a current character, where the current character is a member of the set of characters; interpreting the user's brain signals as one of an "up-signal," a "down-signal," and a "stay-signal"; and receiving a "complete-signal" indicating that all desired characters have been indicated and the ordered set of desired characters is a desired search query.

A set of ordered characters are stored in a database within the memory of the system. The ordered characters are ordered in that they are in a specific sequence. A preferred set of ordered characters is the alphabet or the alphabet along with numbers and a space. The "current character" is a pre-selected character from within the set of ordered characters. The current character is a character that the user will manipulate into a desired character, likely the first character, of a search query. The characters that the user selects as part of his search query are "desired characters." The result of a user completing adding desired characters to his search query is a "desired search query," on which the system will search. The current character is pre-selected by either the user or the system. When the preferred alphabet is used as the set of ordered characters, the preferred current character is "A."

A user's brain signals may be interpreted as one of an up-signal, a down-signal, and a stay-signal. An up-signal indicates the user's desire to move away from the current character through the sequence of the set of ordered characters in one direction. A down-signal indicates the user's desire to move away from the current character through the sequence of the set of ordered characters in the other direction. Up-signals and down-signals preferably indicate a desire to move one character away from the current character within the set of ordered characters. A stay-signal, if indicated not in combination with an up-signal or a down-signal, indicates that the current character is the desired character. A stay-signal following an up-signal or down-signal indicates that the character within the set to which the user has moved is the desired character.

Although preferred embodiments include the alphabet as the preferred set of ordered characters, in some embodiments, the set of ordered characters may instead be a dictionary of words, phrases, or n-grams. An n-gram is a contiguous sequence of n items from a given sequence of text or speech. The items may be phonemes, syllables, letters, words, or base pairs. In such embodiments, especially those in which the set of ordered characters includes words or phrases, the desired search may be only one character, i.e. one word or phrase, long. In these instances, once the user has settled on the desired character, he will then indicate a complete-signal, indicating that all desired characters have been entered and the desired character is the desired search query.

In most instances, however, especially those in which the set of ordered characters is the alphabet, the desired search query will be more than one character long. As such, preferred embodiments of the method include the step of adding on to the search query based on characters indicated as desired characters. Once a user has entered a stay-signal, the search query will move to the next character in the search query, and begin again with a current character. The current character may be the same pre-selected current character or it may be the last desired character chosen by the user. In some embodiments, a dictionary of known terms is provided, and the next current character may be the most frequent character to follow the last desired character. In addition, using the dictionary, the set of ordered characters may be narrowed so as to only include characters that follow the last desired character in the dictionary. The user continues adding desired characters in this way until the desired search query has been entered. At that point, the user indicates a complete-signal, indicating that all desired characters have been entered and the search query entered, which is the ordered set of all of the entered desired characters, is the desired search query. Again, in some instances, the ordered set of all the desired characters that have been entered may be a set of one. In most cases, however, where the desired search query includes more than one desired character, the order of the set of desired characters is generally the order in which the user entered the desired characters using the stay-signal.

In addition to, or in place of up-signals and down-signals, some embodiments of the present invention include other methods for moving within the set of ordered characters. For example, the user may "jump" within the set of ordered characters, indicating that the user desires to move more than one position away from the current character. The number of positions of the jump may be predetermined, as n positions, where n is any integer less than the total number of characters included in a set of ordered characters. For example, if the set of ordered characters is the alphabet and the current character is "A" at the beginning of the alphabet, then a jump signal may be predetermined to jump to "M" in the middle of the alphabet. Alternatively, relatively advanced users may indicate a relative position within the set of ordered characters. A user might indicate the middle of the set of ordered characters as a relative position, which might bring the user to within a few characters of the desired character. As another example, the relative position may be indicated by a percentage of the set of ordered characters: If the set of ordered characters is the alphabet, which may be considered a scale of 1 to 100, and the user indicates a desire to go to about 75% of the way through the set of ordered characters, then the corresponding number would be letter number 19 or 20 in the set of ordered characters, which corresponds to the letters "S" or "T." For embodiments that include jumps as described above, the set of current characters may be weighted for frequency to facilitate the user. Using the last example, if the user has indicated a desire to jump about 75% of the way through the alphabet, then the possible letters may be "R," "S," "T," and "U." "R" and "S" have about the same frequency in the English language. "T" is about a third more frequent than "S" or "R," and "U" is about a third as frequent as "T." Therefore once the user has narrowed down the possible characters to these four that are about 75% of the way through the alphabet, the set of ordered characters that only includes these four characters will be weighted roughly ⅜ toward "T," ¼ each toward "S" and "R," and ⅛ toward "U." As such, it will be easiest for the user to then indicate "T" as the desired character because the set is weighted that way. In addition, any of these embodiments may also include a dictionary of known terms, as discussed above. As such, the next current character may be the most frequent character to follow the last desired character. In addition, using the dictionary, the set of ordered characters may be narrowed so as to only include characters that follow the last desired character in the dictionary.

In some embodiments, the step of providing a character ordering and a current character are personalized or customized to a user. For example, the character ordering and current character may be based on letter frequency for a specified language. The character ordering and current character may also be based on the overall frequency of letters the user has input previously. The character ordering and current character may also be based on the user's prior search results. In a variation on this last embodiment, the character ordering and current character may also be based on the frequency of letters of textual content the user has been exposed to. In this case "exposed to" may mean material from the user's prior search results, or content the user has read, clicked on, composed, etc. . . . . . As a final example of how the current character and character ordering may be personalized for a user, the current character and character ordering may be based on the general location in which the user is conducting the search, the general time of day during which the user is conducting the search, or a combination of the two. One of ordinary skill in the art will recognize that the listed examples are but a few means by which a current character or character ordering may be customized or personalized to a user. Other examples, equivalent examples, and examples commonly used in the art are also considered to be within the scope of the present invention.

The step of performing a search may also involve a level of abstraction within an ontology. A search may go from general to specific—a "general-to-specific" search—e.g. the search query is "vehicle" and the search results are "car," "bus," "truck," etc. . . . , which are all specific examples of a vehicle. A search may also go in the reverse to be a "specific-to-general" search. A search may be a meronymy or "contains-relations" search, e.g. the search query is "fingernail" and the search results are "finger," "hand," "arm," etc. . . . , which are all things that include a fingernail. A search may be a holonymy or "part-of-relations" search, which is the opposite of a meronymy, e.g. the search query is "atom" and the search results are "quark," "proton," "electron," etc. . . . , which are all parts of an atom. Finally, a search may be a synonym search, which returns synonyms of the search query, or a search may be an antonym search, which returns antonyms of the search query. A user may switch modes between standard searching and other types of searching, such as ontological searches as described above, using any means commonly used in the art. The user may indicate the switch using brain signals, other body signals, such as eye blinking, or by providing audio or tactile input.

These aspects of the present invention are not meant to be exclusive and other features, aspects, and advantages of the present invention will be readily apparent to those of ordinary skill in the art when read in conjunction with the following description, accompanying drawings, and claims.

DETAILED DESCRIPTION

Figure 1:
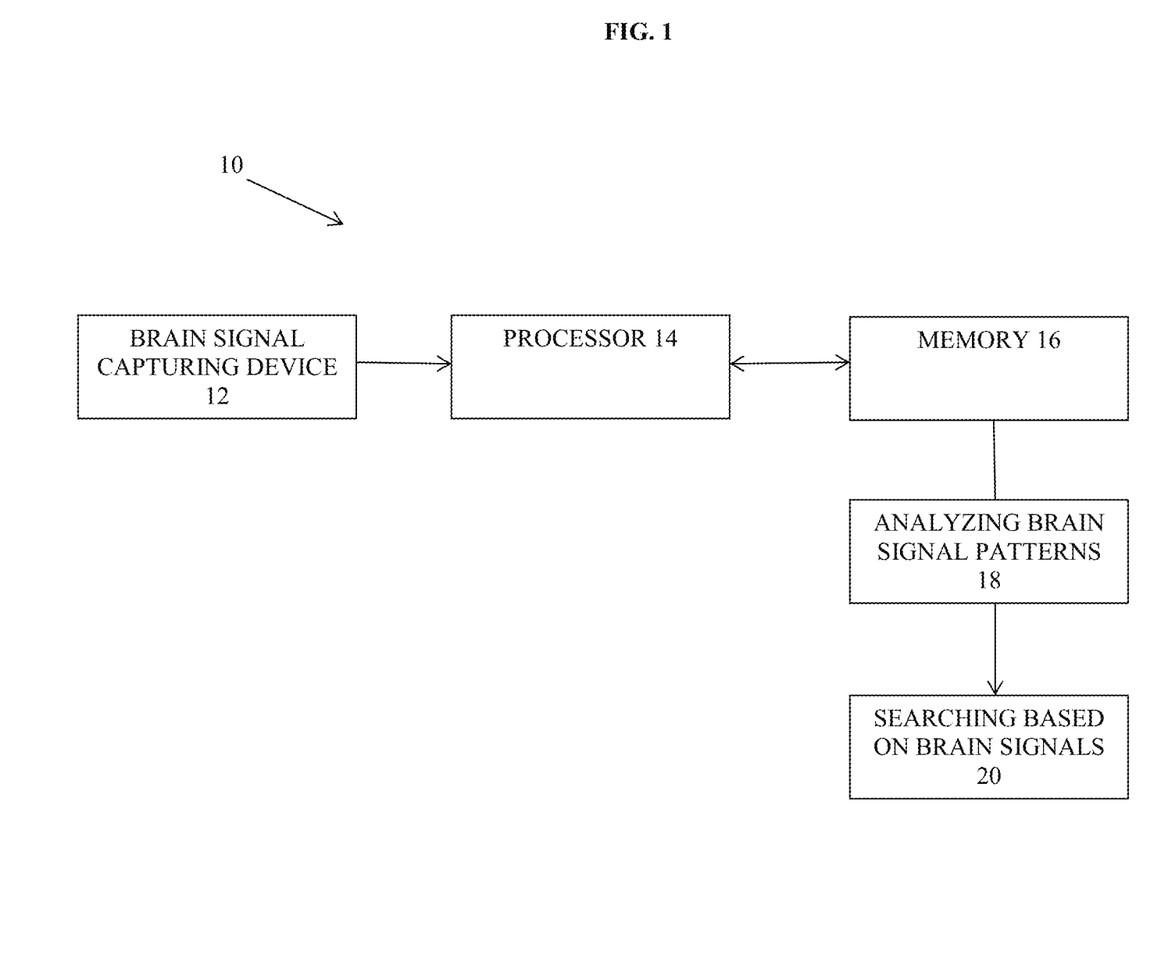
FIG. 1 is a block diagram of the system of the present invention.

Referring first to FIG. 1, a block diagram of system 10 is provided. System 10 includes brain signal capturing device 12, memory device 16 for storing software instructions, and processor 14. The processor 14 is in communication with the brain signal capturing device 12 and executes the instructions stored on the memory 16. The instructions include the steps of analyzing a user's brain signal patterns 18 and searching based on the user's brain signals 20. Processor 14 is preferably part of a mobile device. The step of searching 20 is preferably instant searching.

Figure 2:
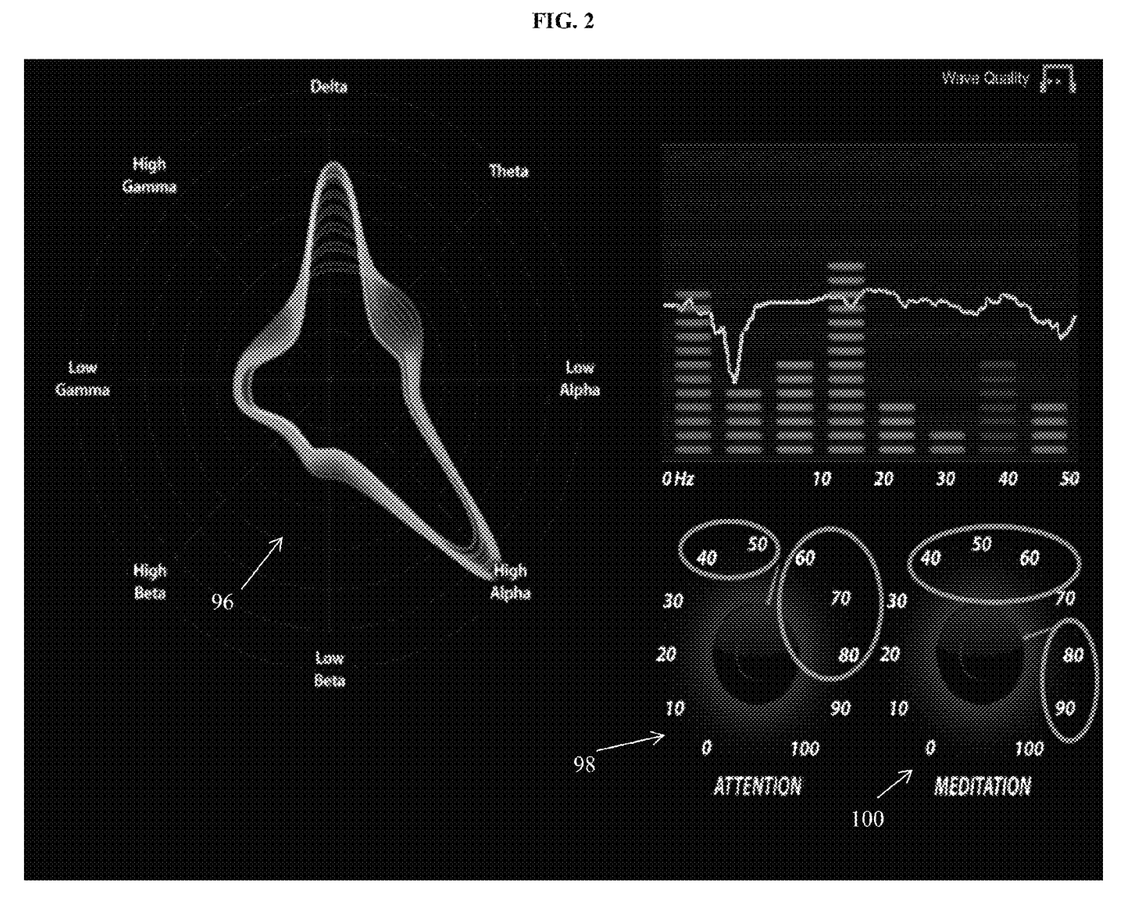
FIG. 2 is a diagram of a measurement of EEG and derived brain signals.

Now referring to FIG. 2, a diagram of a measurement of EEG and derived brain signals is provided. On the left, a graph of an EEG signal 96 is provided. The EEG signal 96 includes several aspects, such as Low Alpha, High Alpha, Low Beta, High Beta, Low Gamma, High Gamma, Delta, and Theta. The EEG signal 96 shown shows a high High Alpha aspect and a relatively high Delta aspect. Derived signals of attention 98 and meditation 100 are also shown on the lower right. Attention 98 and meditation 100 are both on a scale of 1-100.

The present invention uses brain signals, such as EEG 96 and derived signals, attention 98 and meditation 100, to navigate dictionaries or alphanumeric characters. The ability to control CTBCI-estimated human brain metrics may vary widely from user to user. For example, there will be variations in the levels of a metric that a user is able to control. One user may be able to consciously control moving a derived signal or metric, such as attention 98 or meditation 100, through its entire range of 1-100. Another user may only be able to move within a part of the spectrum, 40-90 for instance. There will also be variations in precise targeting within a metric. One user may be able to concentrate on hitting 87, and come within plus or minus 8, for example. Another user may only be able to roughly hit a target, such as concentrating on getting to the upper half of a metric range. There will also be variations in maintaining focus at a certain level. Some users may be able to keep the metric stable for a long period of time, while others may only be able to keep the metric at a certain level for a limited time. There will also be variations in the amount of training or retraining a user may need to be able to control the metrics. Some users may need little to no training to be able to control the metrics with their brain. Others may need a significant amount of training and periodic retraining to be able to control the metrics. There will also be variations in tolerance for distractions when controlling metric levels. When being used in search or other applications, the actions and feedback, e.g. graphical user interface, sounds or speech, vibrations, in the application itself may influence a user's capability to control brain metrics. Some might easily cope with such distractions, while others may have be challenged to control the metrics within an application that might cause mental distractions.

Figure 4:
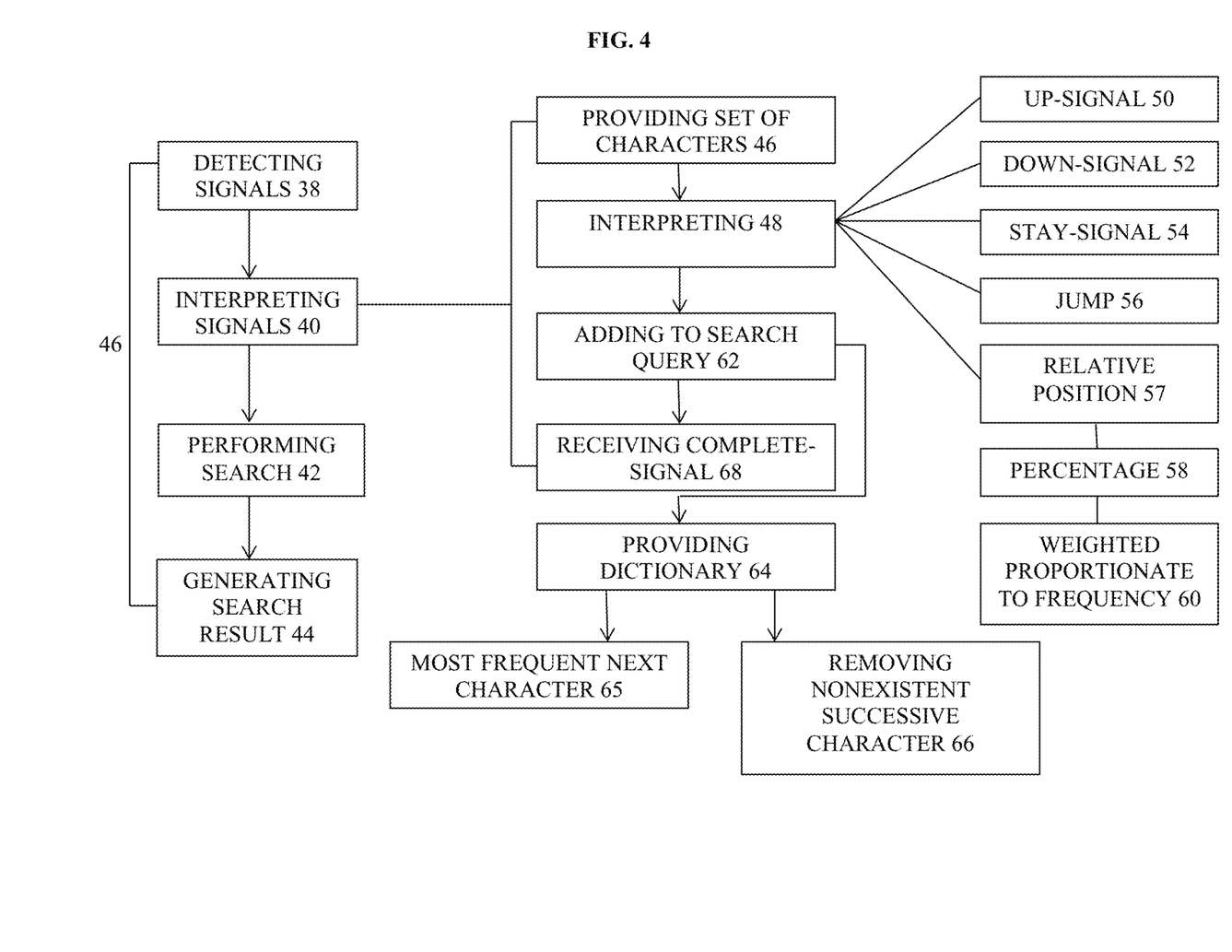
FIG. 4 is a flow chart showing a detail of the searching step.

Despite the fact that there may be broad variations in the ability to control brain metrics 98, 100 from user to user, if the user can obtain even some control of the metrics, he is likely to be able to at least move the metric up or down. Moving a metric up or down corresponds to up-signals 50 and down-signals 52, as shown in FIG. 4, and discussed below. Any user is also likely to have a range of personal zero metric points when resting. As shown in FIG. 2, for example, a user may have a personal zero metric point at 70 for meditation 100, with the ability to move up and down from there within 40-60 (shown in red) and 80-90 (shown in blue), respectively. Using the measured EEG signals 96 and derived signals 98, 100, users can control actions in a relative manner with their brain, i.e. by moving up or down within a metric 98, 100. This ability, along with being able to hold a value, pauses, and frequencies between change of values and strength of values, is used in the present invention to express search queries in several ways described herein.

Figure 3:
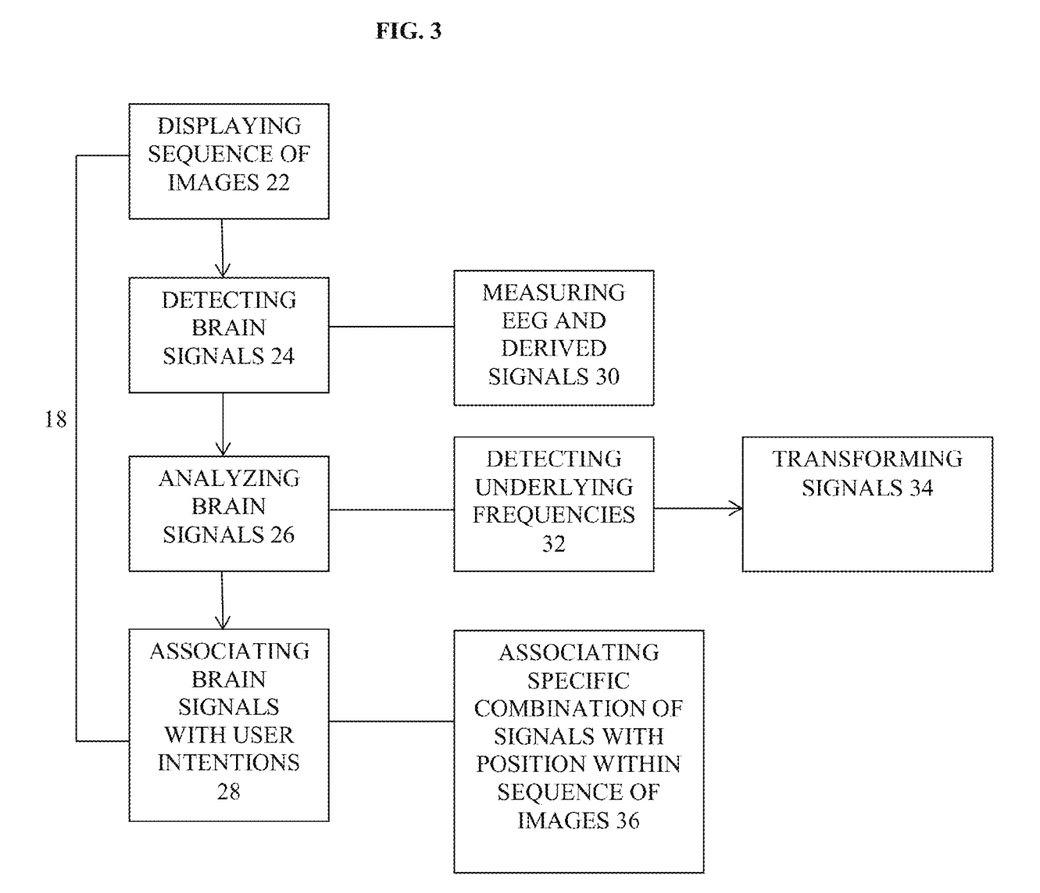
FIG. 3 is a flow chart showing a detail of the analyzing step.

Now referring to FIG. 3, a flow chart showing a detail of the analyzing step 18 is provided. The step of analyzing the user's brain signal patterns 18 includes the steps of displaying to the user a sequence of images 22, detecting the user's brain signals as he views the sequence of images 24, analyzing the user's brain signals 26, and associating the user's brain signals with user intentions 28. The sequence of images may be a sequence of pictures, a sequence of letters, a sequence of words, or any other visual sequence that will promote a measurable and variable response in the user's brain patterns. The step of detecting the user's brain signals 24 preferably includes measuring all EEG signals and derived signals 30 produced by the user and detected by the brain signal capturing device while the user views the sequence of images. The step of analyzing the user's brain signals 26 preferably includes detecting underlying frequencies in the user's brain signals using a Fourier transform 32 and transforming the user's brain signals into even more derived signals using kernel methods 34. The Fourier transform method used is preferably either fast Fourier transform (FFT) or discrete Fourier transform (DFT). The kernel method used is preferably the radical basis function (RBF) kernel.

In further explanation, one continuous brain signal may be expressed as a sum or combination of other simpler signals. An FFT-algorithm finds these simpler underlying signals. As used herein, the term "derived signals" refers to these underlying signals of a detected brain signal as divided from the detected brain signal by a Fourier transform method. An "Attention" signal FFT, for example, may provide several derived signals that, when combined, are the full, original "Attention" signal. As the original "Attention" signal varies over time, the derived signals may also vary. To summarize, the FFT splits a detected brain signal into several other discrete, derived signals.

A kernel method, such as RBF, is a non-linear transformation of data from one dimension into a higher dimension. A kernel transformation may extend two input signals (e.g. $x(t)$, $y(t)$—two values per time unit), into five signals (e.g. $x(t)$, $y(t)$, $x(t)*x(t)$, $x(t)*y(t)$, $y(t)*y(t)$). The objective of such kernel transformations may be to make something that is not linearly separable into something that is linearly separable in a higher dimension. Kernel methods have been used with support vector machines, for example. In machine learning, support vector machines are supervised learning models with associated learning algorithms that analyze data and recognize patters, user for classification and regression analysis. In the present context, the objective in using kernel methods is to extend the number of potential signals within a captured brain signal in order to more easily classify that brain signal, e.g. to classify or predict which letter the user is thinking about.

The step of associating the user's brain signals with user intentions 28 may include associating a specific combination of measured EEG signals and derived signals produced by the user while viewing a specific image in the sequence of images with the position of specific image viewed within the sequence 36. As a user's training consists of mental training on sequences, each element in a sequence, for example a specific letter or image, may be considered a solution—y. All the measured EEG signals 96 and derived metrics 98, 100, which are measured at the time immediately after exposure to a y, are the corresponding vector of x values for that y. Using this vector, the system can find which position— absolute, relative, or approximate—a user is thinking about among a sequence of items, like letters. In the case where the sequence of images is the English alphabet, for example, a specific combination of a low alpha EEG signal 96, and specific attention 98 and meditation 100 signals may imply that the user is thinking about a particular letter position, such as the fifth position, or the letter "E."

Now referring to FIG. 4, a flow chart showing a detail of the searching step 20 is provided. The step of searching based on the user's brain signals 20 includes the steps of detecting the user's brain signals 38, interpreting the user's brain signals as at least one character of a search query 40, performing a search based on the at least one search query 42, and generating a search result 44. The step of detecting the user's brain signals 38 involves the computer or processor receiving the brain signals from the brain signal capturing device. The step of interpreting the user's brain signals as at least one character of a search term 40 preferably includes the steps of providing a set of ordered characters and a current character 46, wherein the current character is a member of the set of characters; interpreting the user's brain signals 48 as one of an up-signal 50, a down-signal 52, and a stay-signal 54; adding on to the search query 62; and receiving a complete-signal 68 indicating that all desired characters have been indicated and the ordered set of desired characters is a desired search query.

A user's brain signals may be interpreted as one of an up-signal 50, a down-signal 52, and a stay-signal 54. An up-signal 50 indicates the user's desire to move away from the current character through the sequence of the set of ordered characters in one direction. For example, if the set of ordered characters is the alphabet and the current character is "A," a user may indicate an up-signal to move forward through the alphabet six positions to the desired character of "H." A down-signal 52 indicates the user's desire to move away from the current character through the sequence of the set of ordered characters in the other direction. For example, if the set of ordered characters is the alphabet and the current character is "A," a user may indicate a down-signal to move backward through the alphabet seven positions to the desired character of "T." The respective directions of the up-signal and down-signal are arbitrary, but always opposite. In other words, in the examples given, it could be a down-signal that goes from the "A" to "H" and an up-signal that goes from "A" to "T." A stay-signal 54, if indicated not in combination with an up-signal 50 or a down-signal 54, indicates that the current character is the desired character. Therefore if "A" is the current character and is also the desired character, the user will not use an up-signal or a down-signal, but rather will indicate a stay-signal. A stay-signal 54 following an up-signal 50 or down-signal 52 indicates that the character within the set to which the user has moved is the desired character. To use an example from above, if the user indicates a down-signal to "T," which is the desired character, the user would then indicate a stay-signal.

Once a user has entered a stay-signal 54, the search query will move to the next character in the search query, and begin again with a current character. The current character may be the same pre-selected current character or it may be the last desired character chosen by the user. In some embodiments, a dictionary of known terms is provided 64, and the next current character may be the most frequent character to follow the last desired character 65. In addition, using the dictionary, the set of ordered characters may be narrowed 66 so as to only include characters that follow the last desired character in the dictionary. The user continues adding desired characters 62 in this way until the desired search query has been entered. At that point, the user indicates a complete-signal 68, indicating that all desired characters have been entered and the search query entered, which is the ordered set of all of the entered desired characters, is the desired search query.

In addition to, or in place of up-signals and down-signals, some embodiments of the present invention include other methods for moving within the set of ordered characters. For example, the user may jump 56 within the set of ordered characters, indicating that the user desires to move more than one position away from the current character. The number of positions of the jump may be predetermined. For example, if the set of ordered characters is the alphabet and the current character is "A" at the beginning of the alphabet, then a jump signal may be predetermined to jump to "M" in the middle of the alphabet. Alternatively, relatively advanced users may indicate a relative position 57 within the set of ordered characters. A user might indicate the middle of the set of ordered characters as a relative position, which might bring the user to within a few characters of the desired character. As another example, the relative position may be indicated by a percentage 58 of the set of ordered characters: If the set of ordered characters is the alphabet, which may be considered a scale of 1 to 100, and the user indicates a desire to go to about 75% of the way through the set of ordered characters, then the corresponding number would be letter number 19 or 20 in the set of ordered characters, which corresponds to the letters "S" or "T." For embodiments that include jumps as described above, the set of current characters may be weighted for frequency 60 to facilitate the user. Using the last example, if the user has indicated a desire to jump about 75% of the way through the alphabet, then the possible letters may be "R," "S," "T," and "U." "R" and "S" have about the same frequency in the English language. "T" is about a third more frequent than "S" or "R," and "U" is about a third as frequent as "T." Therefore once the user has narrowed down the possible characters to these four that are about 75% of the way through the alphabet, the set of ordered characters that only includes these four characters will be weighted roughly ⅜ toward "T," ¼ each toward "S" and "R," and ⅛ toward "U." As such, it will be easiest for the user to then indicate "T" as the desired character because the set is weighted that way. In addition, any of these embodiments may also include a dictionary of known terms, as discussed above. As such, the next current character may be the most frequent character to follow the last desired character. Also, using the dictionary, the set of ordered characters may be narrowed so as to only include characters that follow the last desired character in the dictionary.

Figure 5:
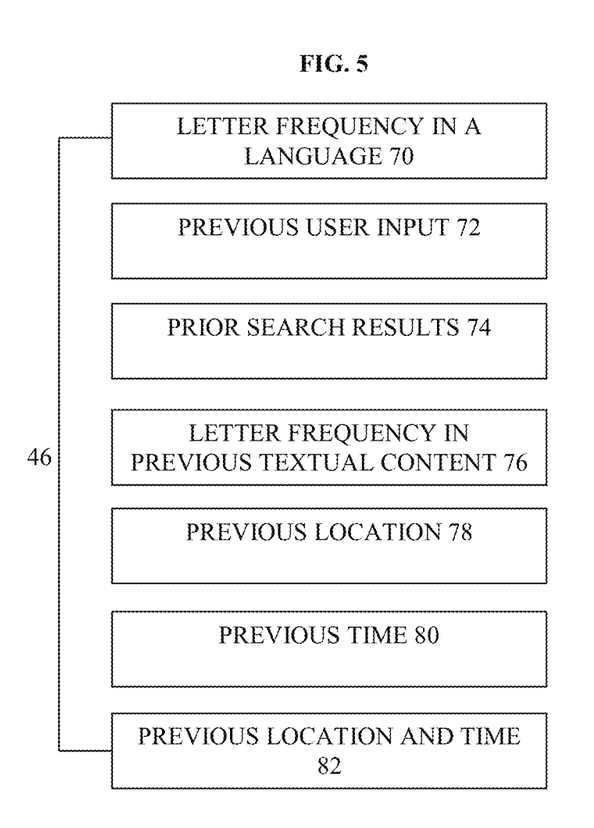
FIG. 5 is a block diagram showing examples of how the step of providing a character ordering and a current character may be personalized or customized.

Now referring to FIG. 5, a block diagram showing examples of how the step of providing a character ordering and a current character 46 may be personalized or customized to a user is provided. For example, the character ordering and current character may be based on letter frequency for a specified language 70. The current character may be selected as the most common first letter of a word in a specified language. In addition, the order of the characters within the set of ordered characters may be in order of letter frequency in a specified language, rather than alphabetical order.

The character ordering and current character may also be based on the overall frequency of letters the user has input previously 72. If the user had searched previously for "Peter picked a peck of pickled peppers," for example, the letter frequency would be E=7, P=7, C=3, K=3, D=2, I=2, R=2, A=1, F=1, L=1, O=1, S=1, and T=1. "E" or "P" may be selected as the current character because they are the most frequently used character. The character ordering in the set of ordered characters based on this prior input by the user may therefore be E P C K D I R A F L O S T. As such P, C, and K are fairly early in the ordering due to their relatively high frequency in the prior input, and A, S, and T are fairly late in the ordering due to their relatively low frequency in the prior input. This is as opposed to the ordering based on frequency in a language overall. If the character ordering were based on the frequency of letters in the English language as discussed above, for example, the characters A, S, and T would be much earlier in the ordering than P, C, and K.

The character ordering and current character may also be based on the user's prior search results 74. If the user has frequently enter search queries, such as "Norway traitor" or "Vidkun," that returned "Quisling," then "Quisling" would be relatively early in a set of ordered characters that are words, or the letters I, G, L, N, U, S, and Q would be relatively early in a set of ordered characters that are letters. In a variation on this last embodiment, the character ordering and current character may also be based on the frequency of letters of textual content 76 that the user has been exposed to. In this case "exposed to" may mean material from the user's prior search results, or content the user has read, clicked on, composed, etc. . . . .

Figure 6:
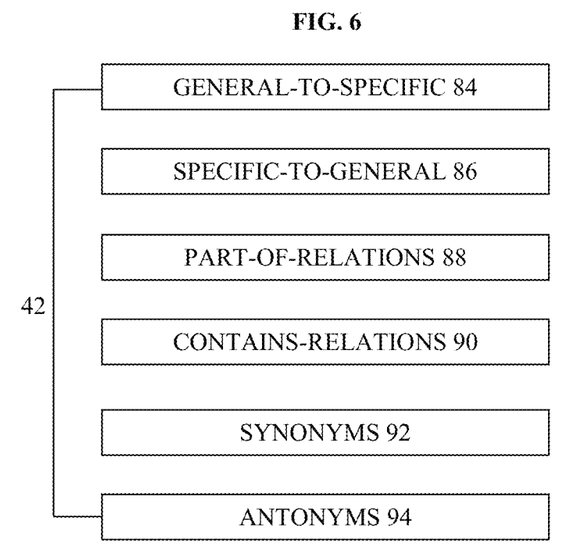
FIG. 6 is a block diagram showing options for performing a search involving a level of abstraction within an ontology.

As a final example of how the current character and character ordering may be personalized for a user, the current character and character ordering may be based on the general location in which the user is conducting the search 78, the general time of day during which the user is conducting the search 80, or a combination of the two 82. For example, if the user frequently searches for "mcdonalds" when he is at Columbus Avenue and 38$^{th}$ Street, then when the user commences a search near or at that location, the word "mcdonalds" will be relatively early in the ordering of a set of ordered characters that are words, or the letters in "mcdonalds" will be relatively early in a set of ordered characters that are letters. Similarly, if a user frequently searches for "happy hour specials" at around 4:30 pm, then when the user commences a search near or at that time of day, "happy hour specials" or the letters therein will be relatively early in the set of ordered characters. Finally, if a user frequently searches for "sunrise Atlanta" at 5 am when he is in Atlanta, Ga., then when the user commences a search at about the same time in Atlanta, "sunrise Atlanta" will be relatively early in the set of ordered characters. Now referring to FIG. 6, a block diagram showing options for performing a search 42 involving a level of abstraction within an ontology is provided. A search may go from general to specific—a "general-to-specific" search—e.g. the search query is "vehicle" and the search results are "car," "bus," "truck," etc. . . . , which are all specific examples of a vehicle. A search may also go in the reverse to be a "specific-to-general" search. A search may be a meronymy or "contains-relations" search, e.g. the search query is "fingernail" and the search results are "finger," "hand," "arm," etc. . . . , which are all things that include a fingernail. A search may be a holonymy or "part-of-relations" search, which is the opposite of a meronymy, e.g. the search query is "atom" and the search results are "quark," "proton," "electron," etc. . . . , which are all parts of an atom. Finally, a search may be a synonym search, which returns synonyms of the search query, or a search may be an antonym search, which returns antonyms of the search query.

The search techniques described above may be applied for searching directly in documents. If searching on the title of a document, the ordering of the words within the title matters for search efficiency. In general, the lowest frequency terms are more informative than the higher frequency terms. Stopwords, for example, are high frequency, but add little information. Six different ways to search for the title, "Winnie the Poo" are introduced below, each of which are supported with the search techniques described above. Assuming that the titles are sorted alphabetically, the within-title sorting alters the navigation and search experience significantly. Examples of title orderings for "Winnie the Poo":

winnie the poo→title
poo winnie the→title sorted, stopword at the end
poo the winnie→title sorted alphabetically
the poo winnie→title sorted according to word frequency (highest first)
winnie poo the→title inversely sorted according to word frequency (lowest first)
winnie poo→title omitting stopword "the"

Although the present invention has been described in considerable detail with reference to certain preferred versions thereof, other versions would be readily apparent to those of ordinary skill in the art. Therefore, the spirit and scope of the description should not be limited to the description of the preferred versions contained herein.

I claim:

1. A system comprising:
   at least one brain signal capturing device capable of detecting a user's brain signals;
   at least one memory device storing instructions; and
   at least one processor wherein said at least one processor is in communication with said at least one brain signal capturing device and executes said instructions, said instructions comprising the steps of:
   analyzing brain signal patterns created by a brain of the user, comprising the steps of:
      displaying to the user a sequence of images;
      detecting the user's brain signals as the user views the sequence of images, comprising measuring all EEG signals and derived signals produced by the user and detected by said at least one brain signal capturing device while the user views the sequence of images;
      analyzing the user's brain signals; and
      associating the user's brain signals with user intentions, and;
   creating a text-based search inquiry based on the user's brain signals.

2. The system as claimed in claim 1, wherein said at least one brain signal capturing device comprises a headset.

3. The system as claimed in claim 1, wherein said step of analyzing the user's brain signals comprises the steps of:
   detecting underlying frequencies in the user's brain signals using a Fourier transform; and
   transforming the user's brain signals into additional derived signals using kernel methods.

4. The system as claimed in claim 1, wherein said step of associating the user's brain signals with user intentions comprises associating a specific combination of measured EEG signals and derived signals produced by the user and detected by said at least one brain signal capturing device while the user views a specific image in the sequence of images with a position of the specific image being viewed by the user within the sequence of images when the specific combination of measured EEG signals and derived signals is measured.

5. The system as claimed in claim 1, wherein the step of creating a text-based search inquiry based on the user's brain signals comprises:
  detecting the user's brain signals;
  interpreting the user's brain signals as at least one character of a search query;
  performing a search based on the search query; and
  generating a search result.

6. The system as claimed in claim 5, wherein said at least one memory device further stores a database, and wherein said step of interpreting the user's brain signals as at least one character of a search query comprises the steps of:
  providing a set of ordered characters and a current character, wherein the current character is a member of the set of ordered characters, and the set of ordered characters is stored in said database;
  interpreting the user's brain signals as one of an up-signal, indicating a desire to move in a first direction within the set of ordered characters away from the current character toward a desired character; a down-signal, indicating a desire to move in a second direction within the set of ordered characters away from the current character toward a desired character; and a stay-signal indicating that the current character is a desired character; and
  receiving a complete-signal indicating that all desired characters have been indicated and an ordered set of desired characters is a desired search query.

7. The system as claimed in claim 6, further comprising the step of adding on to the search query based on characters indicated as desired characters.

8. The system as claimed in claim 6, wherein said step of interpreting the user's brain signals as at least one character of a search query further comprises the step of providing a character ordering within the set of ordered characters and the current character, and wherein the character ordering is based on letter frequency for a specified language.

9. The system as claimed in claim 6, wherein said step of interpreting the user's brain signals as at least one character of a search query further comprises the step of providing a character ordering within the set of ordered characters and the current character, and wherein the character ordering is based on an overall frequency of letters the user has input previously.

10. The system as claimed in claim 6, wherein said step of interpreting the user's brain signals as at least one character of a search query further comprises the step of providing a character ordering within the set of ordered characters and the current character, and wherein the character ordering is based on the user's prior search results.

11. The system as claimed in claim 6, wherein said step of interpreting the user's brain signals as at least one character of a search query further comprises the step of providing a character ordering within the set of ordered characters and the current character, and the character ordering is based on a frequency of letters of textual content the user has been exposed to.

12. The system as claimed in claim 6, wherein said system further comprises a device capable of geolocation that is in communication with said at least one processor, and said step of interpreting the user's brain signals as at least one character of a search query further comprises the steps of:
  determining a location of the user from said device capable of geolocation; and
  providing a character ordering within the set of ordered characters and the current character, and wherein the character ordering is based on what search input the user has provided in a same location as the user is currently searching.

13. The system as claimed in claim 6, wherein said step of interpreting the user's brain signals as at least one character of a search query further comprises the step of providing a character ordering within the set of ordered characters and the current character, and wherein the character ordering is based on what search input the user has provided at a same time of day as the user is currently searching.

14. The system as claimed in claim 6, wherein said system further comprises a device capable of geolocation that is in communication with said at least one processor, and said step of interpreting the user's brain signals as at least one character of a search query further comprises the steps of:
  determining a location of the user from said device capable of geolocation; and
  providing a character ordering within the set of ordered characters and the current character, and wherein the character ordering is based on what input the user has provided in a same location and at a same time of day as the user is currently searching.

15. The system as claimed in claim 6, wherein said step of interpreting the user's brain signals as at least one character of a search query further comprises the steps of:
  providing a dictionary of known terms; and
  after said step of interpreting the user's brain signals as a stay-signal, removing characters from the set of ordered characters that do not exist as successive characters to the desired character in any known term in the dictionary.

16. The system as claimed in claim 6, wherein the up-signal indicates a desire to move in a first direction within the set of ordered characters away one character from the current character toward the desired character and the down-signal indicates a desire to move in a second direction within the set of ordered characters away one character from the current character toward the desired character.

17. The system as claimed in claim 16, further comprising the step of interpreting the user's brain signals as a jump within the set of ordered characters, wherein the jump indicates a desire to change the current character to a character more than one character away from the current character.

18. The system as claimed in claim 17, wherein:
  the set of ordered characters is alphabetical;
  the current character is at a beginning of the set of ordered characters; and
  the jump indicates a desire to change the current character at the beginning of the set of ordered characters to a character in a middle of the set of ordered characters.

19. The system as claimed in claim 6, wherein said step of interpreting the user's brain signals as at least one character of a search query further comprises the step of interpreting the user's brain signals as an indication of relative position within the set of ordered characters of a desired character.

20. The system as claimed in claim 19, wherein said step of interpreting the user's brain signals as an indication of relative position within the set of ordered characters of a desired character comprises interpreting the user's brain signals as an indication of an approximate percentage of a way through the set of ordered characters wherein the desired character is located within the set of ordered characters.

21. The system as claimed in claim 19, wherein each character of the set of ordered characters is weighted proportionate to a frequency of a use of the character in a specific language.

22. The system as claimed in claim 6, wherein said step of providing a set of ordered characters and a current character, wherein the current character is a member of the set of characters comprises providing a set of one of a group consisting of words, phrases, and n-grams and a one of a group consisting of a current word, current phrase, and current n-gram, wherein the current word, current phrase, or current n-gram is a member of the set of words, phrases, or n-grams, respectively.

23. The system as claimed in claim 5, wherein said step of performing a search based on the search query comprises performing a general-to-specific search.

24. The system as claimed in claim 5, wherein said step of performing a search based on the search query comprises performing a specific-to-general search.

25. The system as claimed in claim 5, wherein said step of performing a search based on the search query comprises performing a part-of-relations search.

26. The system as claimed in claim 5, wherein said step of performing a search based on the search query comprises performing a contains-relations search.

27. The system as claimed in claim 5, wherein said step of performing a search based on the search query comprises performing a synonym search.

28. The system as claimed in claim 5, wherein said step of performing a search based on the search query comprises performing an antonym search.

29. The system as claimed in claim 1, wherein said at least one brain signal capturing device is further capable of detecting motion signals of the user.

30. A system comprising:
at least one brain signal capturing device capable of detecting a user's brain signals;
at least one memory device storing instructions and a database; and
at least one processor wherein said at least one processor is in communication with said at least one brain signal capturing device and executes said instructions, said instructions comprising the steps of:
analyzing brain signal patterns created by a brain of the user, and;
creating a text-based search inquiry based on the user's brain signals, comprising the steps of:
detecting the user's brain signals;
interpreting the user's brain signals as at least one character of a search query, comprising the steps of:
providing a set of ordered characters and a current character, wherein the current character is a member of the set of ordered characters, and the set of ordered characters is stored in said database;
interpreting the user's brain signals as one of an up-signal, indicating a desire to move in a first direction within the set of ordered characters away from the current character toward a desired character; a down-signal, indicating a desire to move in a second direction within the set of ordered characters away from the current character toward a desired character; and a stay-signal indicating that the current character is a desired character; and
receiving a complete-signal indicating that all desired characters have been indicated and an ordered set of desired characters is a desired search query;
performing a search based on the search query; and
generating a search result.

31. The system as claimed in claim 30, wherein said at least one brain signal capturing device comprises a headset.

32. The system as claimed in claim 30, wherein said step of analyzing the user's brain signal patterns comprises the steps of:
displaying to the user a sequence of images;
detecting the user's brain signals as the user views the sequence of images;
analyzing the user's brain signals; and
associating the user's brain signals with user intentions.

33. The system as claimed in claim 32, wherein:
said step of detecting the user's brain signals as the user views the sequence of images comprises measuring all EEG signals and derived signals produced by the user and detected by said at least one brain signal capturing device while the user views the sequence of images;
said step of analyzing the user's brain signals comprises the steps of:
detecting underlying frequencies in the user's brain signals using a Fourier transform; and
transforming the user's brain signals into additional derived signals using kernel methods; and
said step of associating the user's brain signals with user intentions comprises associating a specific combination of measured EEG signals and derived signals produced by the user and detected by said at least one brain signal capturing device while the user views a specific image in the sequence of images with a position of the specific image being viewed by the user within the sequence of images when the specific combination of measured EEG signals and derived signals is measured.

34. The system as claimed in claim 30, further comprising the step of adding on to the search query based on characters indicated as desired characters.

35. The system as claimed in claim 30, wherein said step of interpreting the user's brain signals as at least one character of a search query further comprises the step of providing a character ordering within the set of ordered characters and the current character, and wherein the character ordering is based on letter frequency for a specified language.

36. The system as claimed in claim 30, wherein said step of interpreting the user's brain signals as at least one character of a search query further comprises the step of providing a character ordering within the set of ordered characters and the current character, and wherein the character ordering is based on an overall frequency of letters the user has input previously.

37. The system as claimed in claim 30, wherein said step of interpreting the user's brain signals as at least one character of a search query further comprises the step of providing a character ordering within the set of ordered characters and the current character, and wherein the character ordering is based on the user's prior search results.

38. The system as claimed in claim 30, wherein said step of interpreting the user's brain signals as at least one character of a search query further comprises the step of providing a character ordering within the set of ordered characters and the current character, and the character ordering is based on a frequency of letters of textual content the user has been exposed to.

39. The system as claimed in claim 30, wherein said system further comprises a device capable of geolocation that is in communication with said at least one processor, and said step of interpreting the user's brain signals as at least one character of a search query further comprises the steps of:
   determining a location of the user from said device capable of geolocation; and
   providing a character ordering within the set of ordered characters and the current character, and wherein the character ordering is based on what search input the user has provided in a same location as the user is currently searching.

40. The system as claimed in claim 30, wherein said step of interpreting the user's brain signals as at least one character of a search query further comprises the step of providing a character ordering within the set of ordered characters and the current character, and wherein the character ordering is based on what search input the user has provided at a same time of day as the user is currently searching.

41. The system as claimed in claim 30, wherein said system further comprises a device capable of geolocation that is in communication with said at least one processor, and said step of interpreting the user's brain signals as at least one character of a search query further comprises the steps of:
   determining a location of the user from said device capable of geolocation; and
   providing a character ordering within the set of ordered characters and the current character, and wherein the character ordering is based on what input the user has provided in a same location and at a same time of day as the user is currently searching.

42. The system as claimed in claim 30, wherein said step of interpreting the user's brain signals as at least one character of a search query further comprises the steps of:
   providing a dictionary of known terms; and
   after said step of interpreting the user's brain signals as a stay-signal, removing characters from the set of ordered characters that do not exist as successive characters to the desired character in any known term in the dictionary.

43. The system as claimed in claim 30, wherein the up-signal indicates a desire to move in a first direction within the set of ordered characters away one character from the current character toward the desired character and the down-signal indicates a desire to move in a second direction within the set of ordered characters away one character from the current character toward the desired character.

44. The system as claimed in claim 43, further comprising the step of interpreting the user's brain signals as a jump within the set of ordered characters, wherein the jump indicates a desire to change the current character to a character more than one character away from the current character.

45. The system as claimed in claim 44, wherein:
   the set of ordered characters is alphabetical;
   the current character is at a beginning of the set of ordered characters; and
   the jump indicates a desire to change the current character at a beginning of the set of ordered characters to a character in a middle of the set of ordered characters.

46. The system as claimed in claim 30, wherein said step of interpreting the user's brain signals as at least one character of a search query further comprises the step of interpreting the user's brain signals as an indication of relative position within the set of ordered characters of a desired character.

47. The system as claimed in claim 46, wherein said step of interpreting the user's brain signals as an indication of relative position within the set of ordered characters of a desired character comprises interpreting the user's brain signals as an indication of an approximate percentage of a way through the set of ordered characters wherein the desired character is located within the set of ordered characters.

48. The system as claimed in claim 46, wherein each character of the set of ordered characters is weighted proportionate to a frequency of a use of the character in a specific language.

49. The system as claimed in claim 30, wherein said step of providing a set of ordered characters and a current character, wherein the current character is a member of the set of characters comprises providing a set of one of a group consisting of words, phrases, and n-grams and a one of a group consisting of a current word, current phrase, and current n-gram, wherein the current word, current phrase, or current n-gram is a member of the set of words, phrases, or n-grams, respectively.

50. The system as claimed in claim 30, wherein said step of performing a search based on the search query comprises performing a general-to-specific search.

51. The system as claimed in claim 30, wherein said step of performing a search based on the search query comprises performing a specific-to-general search.

52. The system as claimed in claim 30, wherein said step of performing a search based on the search query comprises performing a part-of-relations search.

53. The system as claimed in claim 30, wherein said step of performing a search based on the search query comprises performing a contains-relations search.

54. The system as claimed in claim 30, wherein said step of performing a search based on the search query comprises performing a synonym search.

55. The system as claimed in claim 30, wherein said step of performing a search based on the search query comprises performing an antonym search.

56. The system as claimed in claim 30, wherein said at least one brain signal capturing device is further capable of detecting motion signals of the user.

* * * * *